(12) United States Patent
Batchelor et al.

(10) Patent No.: US 10,561,433 B2
(45) Date of Patent: Feb. 18, 2020

(54) FORCEPS JAW MECHANISM

(71) Applicant: GYRUS ACMI, INC., Southborough, MA (US)

(72) Inventors: Kester J. Batchelor, Mound, MN (US); Eric J. Boone, Saint Michael, MN (US); Christian J. Fiksen, Maple Grove, MN (US); Hanam Sota Pham, Minneapolis, MN (US); Zane Ward, Prior Lake, MN (US); Jeffrey J. Nelson, Plymouth, MN (US); John R. Mensch, Plymouth, MN (US); William Butler, Minneapolis, MN (US); William F. Kratoska, Plymouth, MN (US); Riyad E. Moe, Madison, WI (US)

(73) Assignee: Gyrus Acmi, Inc., Southborough, MA (US)

( * ) Notice: Subject to any disclaimer, the term of this patent is extended or adjusted under 35 U.S.C. 154(b) by 316 days.

(21) Appl. No.: 15/402,741

(22) Filed: Jan. 10, 2017

(65) Prior Publication Data

US 2017/0196579 A1 Jul. 13, 2017

Related U.S. Application Data

(60) Provisional application No. 62/277,010, filed on Jan. 11, 2016, provisional application No. 62/327,534, filed on Apr. 26, 2016.

(51) Int. Cl.
*A61B 17/28* (2006.01)
(52) U.S. Cl.
CPC ........ *A61B 17/2841* (2013.01); *A61B 17/282* (2013.01)

(58) Field of Classification Search
CPC ... A61B 17/2841; A61B 17/282; A61B 17/29; A61B 18/1442; A61B 2018/1455;
(Continued)

(56) References Cited

U.S. PATENT DOCUMENTS 5,172,700 A 12/1992 Bencini et al.
5,637,110 A * 6/1997 Pennybacker ..... A61B 18/1445
606/170
(Continued)

FOREIGN PATENT DOCUMENTS

| JP | 2011-504794 A | 2/2011 |
| WO | 2008/005411 A2 | 1/2008 |
| WO | 2008/008457 A2 | 1/2008 |

OTHER PUBLICATIONS

International Search Report for PCT Application No. PCT/US2017/012838, dated Apr. 3, 2017.
(Continued)

*Primary Examiner* — Erich G Herbermann
(74) *Attorney, Agent, or Firm* — Schwegman Lundberg & Woessner, P.A.

(57) ABSTRACT

An instrument that includes an outer member, an inner member, and a jaw assembly. The inner member includes a first arm and a second arm. The jaw assembly includes a first jaw and a second jaw. The first jaw is connected to the first arm at a first pivot joint and to the outer member at a second pivot joint. The second jaw is connected to the second arm at a third pivot joint and to the outer member at a fourth pivot joint. The inner member is adapted to be moved distally relative to the outer member so that the first jaw pivots about the second pivot joint towards the second jaw and the second jaw pivots about the fourth pivot joint towards the first jaw thus moving the jaw assembly from the open position towards the closed position.

18 Claims, 4 Drawing Sheets

(58) Field of Classification Search
CPC ...... A61B 2017/294; A61B 2017/2939; A61B 2017/2937; A61B 2017/2902
See application file for complete search history.

(56) References Cited

U.S. PATENT DOCUMENTS

| | | | |
|---|---|---|---|
| 5,964,780 A | 10/1999 | Balazs | |
| 6,139,508 A * | 10/2000 | Simpson | A61B 10/06 600/564 |
| 8,672,935 B2 | 3/2014 | Okada et al. | |
| 9,332,988 B2 | 5/2016 | Adams et al. | |
| 9,480,522 B2 | 11/2016 | Horner et al. | |
| 9,668,808 B2 | 6/2017 | Ourada | |
| 2008/0015566 A1 | 1/2008 | Livneh | |
| 2009/0054894 A1 | 2/2009 | Yachi | |
| 2009/0138006 A1 | 5/2009 | Bales et al. | |
| 2010/0160940 A1* | 6/2010 | Lutze | A61B 17/29 606/170 |
| 2011/0184405 A1* | 7/2011 | Mueller | A61B 18/1445 606/41 |
| 2013/0085516 A1 | 4/2013 | Kerr et al. | |
| 2013/0178852 A1 | 7/2013 | Allen, IV et al. | |
| 2014/0171939 A1 | 6/2014 | Yates | |

OTHER PUBLICATIONS

Written Opinion of the International Searching Authority for PCT Application No. PCT/US2017/012838, dated Apr. 3, 2017.
Japanese Office Action for Japanese Patent Application No. 2018-536121; dated Apr. 9, 2019.
"European Application Serial No. 17702194.6, Communication Pursuant to Article 94(3) EPC dated Oct. 31, 2019", 6 pgs.

* cited by examiner

FORCEPS JAW MECHANISM

FIELD

These teachings relate to an instrument, and more particularly to mechanisms for moving forceps between an open position and a closed position.

BACKGROUND

Forceps are plies-like instruments that have opposing jaws. The jaws can be used during a medical procedure to effect an anatomical feature, such as a vessel or tissue. For example, a vessel or tissue can be positioned between the gripping sections of the opposing jaws, and the jaws can be used to move, grip, grasp, push, pull, cut, dissect and/or otherwise effect the vessel or tissue. Some forceps also include electrosurgical capabilities for electrically effecting an anatomical feature.

Jaws of the forceps are typically moveable between an open position and a closed position. Some forceps, such as those disclosed in US 2009/0054894, US 2013/0178852, U.S. Pat. Nos. 8,672,935, 9,332,988, and WO 2008/005411, which are hereby incorporated by reference herein for all purposes, include various features, such as sliding joints, cams, slots, joints, and push rods, for moving the jaws between an open and dosed position. These features may, however, increase the number of components in the forceps; increase the time required to assemble the forceps; and/or may result in failure if the forceps are dropped or mishandled, for example. Moreover, sliding joints, such as cams, can be more complicated to assemble and, when subjected to repeated use, may not be as strong or durable.

Improvement in the art may therefore be desired. For example, it may be advantageous to have forceps with features for moving the jaws between the open position and the closed position that are less complicated and more durable than what is known in the art.

SUMMARY

Advantageously, these teachings provide forceps that include a jaw assembly that is moveable between an open position and a closed position. The forceps include a single, moveable member that is adapted to be advanced and retracted relative to a hand piece of the forceps to move the jaw assembly between an open position and a closed position, and between a dosed position and an open position. The single moveable member is received in an outer member of the forceps, and the outer member does not move relative to a hand piece of the instrument. The single moveable member reduces part count and simplifies assembly of the forceps. The moveable member has high beam strength so that the jaws can be moved without the moveable member bending or breaking as may occur when forceps include push rods for moving the jaw assembly. The moveable member has high beam strength to provide higher jaw closing forces and/or more reliable jaw closing forces as may be the case in instruments lacking such a member.

These teachings provide an instrument that includes a hand piece, an outer member, an inner member, and a jaw assembly. The hand piece includes a lever; a handle; and an actuation mechanism. The inner member includes a first moveable arm; and a second moveable arm. The jaw assembly includes a first jaw and a second jaw. The first jaw is connected to the first arm at a first pivot joint, the first jaw is connected to the outer member at a second pivot joint. The second jaw is connected to the second arm at a third pivot joint, the second jaw is connected to the outer member at a fourth pivot joint. That is, the first pivot joint and the third pivot joint may be a single pivot joint or may be the same pivot joint. The instrument includes an actuation mechanism that converts proximal movement of the lever relative to the handle into distal movement of the inner member so that the first jaw pivots about the second pivot joint towards the second jaw and the second jaw pivots about the fourth pivot joint towards the first jaw thus moving the jaw assembly from the open position to the closed position.

These teachings also provide an instrument that includes a hand piece, an outer member, an inner member, and a jaw assembly. The hand piece includes a lever; a handle; and an actuation mechanism. The outer member includes a first moveable arm; and a second moveable arm. The jaw assembly is moveable between an open position and a closed position. The jaw assembly includes a first jaw and second jaw. The first jaw is connected to the first arm at a first pivot joint, the first jaw is connected to the inner member at a second pivot joint. The second jaw is connected to the second arm at a third pivot joint, the second jaw is connected to the inner member at a fourth pivot joint. The actuation mechanism converts proximal movement of the lever relative to the handle into proximal movement of the inner member so that the first jaw pivots about the first pivot joint towards the second jaw and the second jaw pivots about the third pivot joint towards the first jaw thus moving the jaw assembly from the open position to the closed position.

DETAILED DESCRIPTION

Figure 1:
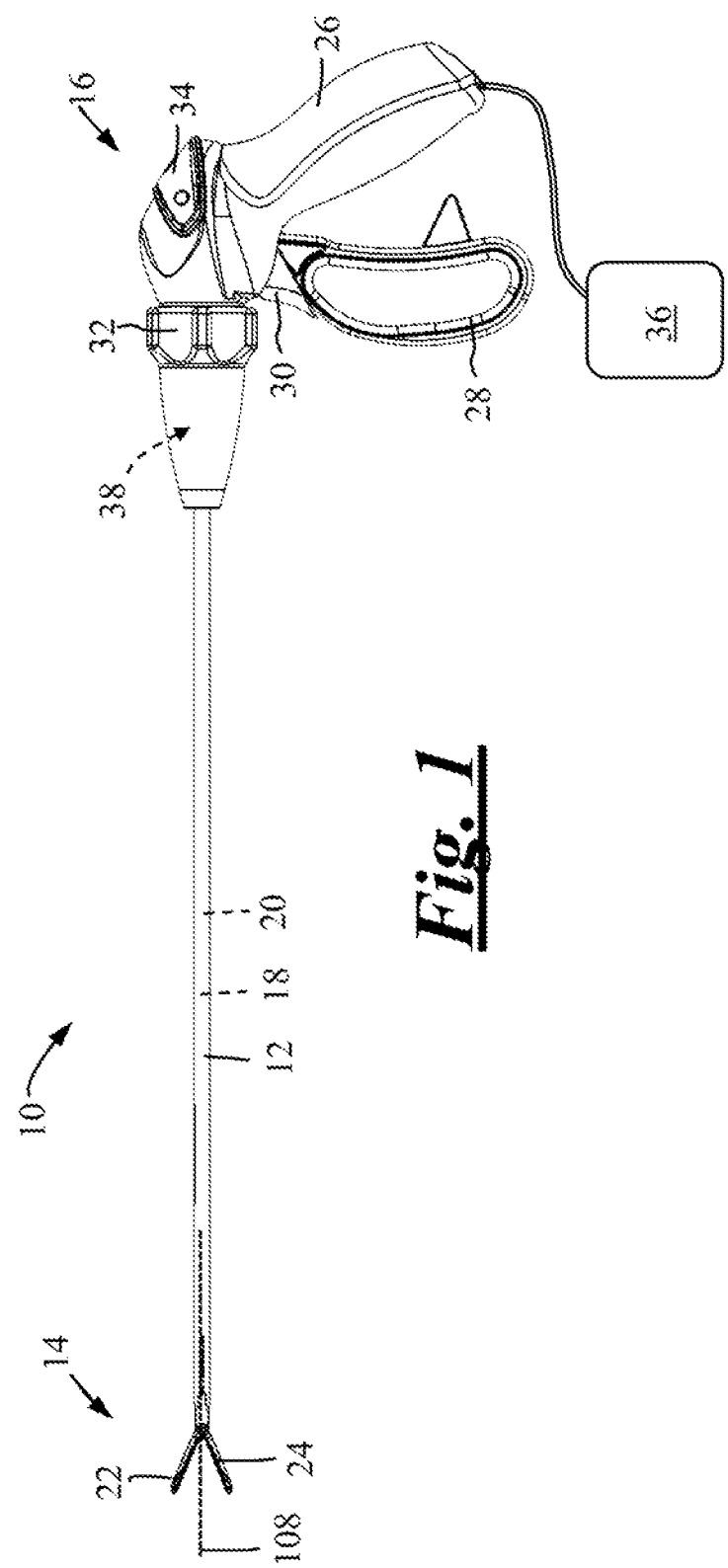
FIG. 1 is a side view of the instrument.

This disclosure claims the benefit of U.S. Provisional Patent Application No. 62/277,010 filed on Jan. 11, 2016, and the benefit of U.S. Provisional Patent Application No. 62/327,534 filed on Apr. 26, 2016, both of which are hereby incorporated by reference herein for all purposes.

Instrument. The present teachings provide an instrument. The instrument can be any instrument used for effecting an object. Effecting may mean, far example: manipulating, engaging, moving, gasping, gripping, pushing, pulling, cutting, tearing, coagulating, sealing, cauterizing, dissecting, fulgurating, or otherwise effecting an object or anatomical feature. The object may be any object, whether an anatomical feature or not. The anatomical feature may be, for example, a vessel, tissue, vein, artery, any portion of the anatomy, or a combination thereof.

The instrument can be used in medically related procedures or in non-medically related procedures. The instrument can be used in open and/or in laparoscopic procedures or minimally invasive procedures. The instrument can be medical forceps, cutting forceps, electrosurgical forceps, bipolar forceps, the like, or a combination thereof.

The instrument may be used with or without power. When used with power, the instrument can be used in electrosurgery. The instrument can be in electrical communication with a suitable power source so that the instrument can be used in a monopolar circuit, a bipolar circuit, or both. The instrument may be used with monopolar energy, bipolar energy, blended energy, or a combination thereof provided by a power source. For example, a suitable current, therapy, and/or signal provided by a power source can be passed from, though, or between, one or more of the jaws, gripping sections, electrically conductive sections, electrodes, a remote pad, a patient or anatomy, or a combination thereof so that an object or anatomical feature can electrically effected.

Hand piece. The instrument may include a hand piece. The hand piece may function to house, support, and/or contain one or more components of the instrument. For example, the hand piece may house, support, and/or contain the parts or components required to move or actuate the inner member, move or actuate the jaw assembly, move or actuate the one or more jaws, move or actuate the cut blade, or a combination thereof. The hand piece may house, support, and/or contain the parts or components required for the electrosurgical functions of the instrument.

The instrument, the hand piece, or both may include sufficient controls for operating, actuating, and/or manipulating the instrument. One or more of these controls may be used to open/close the jaw assembly; move one or more of the jaws towards or away from one another; rotate the jaw assembly; advance or retract the jaw assembly; advance or retract the inner member; advance or retract a cut blade; rotate a cut blade; apply a therapy current; or a combination thereof. The controls may be a wheel, a trigger, a lever, a button, the like, or a combination thereof.

For example, the wheel may be adapted to be moved or manipulated to rotate the jaw assembly about a longitudinal axis of the Jaw assembly, the tubular member, or both. For example, the trigger may be adapted to be moved or manipulated so that the cut blade is translated or reciprocated about the longitudinal axis of the cut blade, the tubular member, the jaw assembly, or a combination thereof. For example, the button may be adapted to be moved or manipulated so that a therapeutic current or signal from the power supply is applied to the jaw assembly, one or both of the jaws, one or more of the gripping sections, one or more electrically conductive sections, one or more of the electrodes, a remote pad, a patient or anatomy, or a combination thereof so that an object or anatomical feature can electrically effected. For example, the lever may be adapted to be moved towards the handle so that the inner member moves proximally relative to the outer member so that the jaw assembly moves from the closed position towards the open position. Alternatively, the inner member may be adapted to move distally relative to the outer member when the lever is moved towards the handle so that so that the jaw assembly moves from the closed position towards the open position. When the lever is moved away from the handle, for example, by releasing the lever, the inner member may move distally relative to the outer member so that the jaw assembly moves from the open position to the closed position. Alternatively, the inner member may move proximally relative to the outer member when the lever is moved away from the handle, for example, by releasing the lever, so that the jaw assembly moves from the open position to the dosed position.

Directions. A longitudinal direction or a longitudinal axis may be a direction or axis along which the outer member, the inner member, the cut blade, or a combination thereof extend.

A vertical direction or a vertical axis may be a direction or axis along which one or both of the jaws move when the jaw assembly is moved between an open and closed position and between a closed position and an open position.

A lateral or transverse direction or a lateral or transverse axis may be a direction or axis that is not a longitudinal direction or a longitudinal axis, and is not a vertical direction or a vertical axis. A lateral or transverse direction or a lateral or transverse axis may be a direction or axis that is perpendicular or orthogonal to both the longitudinal direction or axis and the vertical axis or direction.

The lateral axis or lateral direction, and the vertical axis or vertical direction may be mutually perpendicular, and both of which may be perpendicular to the longitudinal axis or longitudinal direction.

One or both of the jaws may move from an open position to a closed position and back to an open position by moving in a plane, which may be a jaw closing plane that is defined by a longitudinal axis and the vertical axis. The one or more arms of the outer member and/or the one or more anus of the inner member may also move in this plane. This plane can also be defined as a central plane. It is understood that the arms or jaws, may also move along a plane that is coplanar with or parallel to the central plane.

Outer Member. The outer member may function to permit a portion of the instrument to be inserted into a patient or the anatomy, while a portion of the instrument remains outside of the patient or anatomy. The outer member may be configured to be inserted into the anatomy through a trocar. The outer member may allow for the jaw assembly and/or one or more functional elements of the instrument, such as a cut blade, to be manipulated without being impeded by a trocar, the anatomy, or both.

The outer member may be an elongated, tubular member or structure that extends along a longitudinal axis. The outer member may be a tube. The proximal end of the outer member may be fixedly connected to the hand piece so that the outer member is prevented or restricted from being moved or translated independently of the hand piece. The outer member may be substantially straight; may include one or more angles, bends or arcs; or a combination thereof. The outer member may be substantially rigid, substantially bendable flexible, substantially resilient, or a combination thereof.

The outer member may be at least partially hollow and may define therein an inner portion or inner space. The hollow or inner portion or space of the outer member may be sufficiently sized so that one or more jaws, a jaw assembly, a cut blade, an inner member, or a combination thereof can be received in the outer member. The inner member may be received in the outer member such that the two members share a common longitudinal axis. Alternatively, a center longitudinal axis of the inner member may be offset or spaced apart from a center longitudinal axis of the outer member. Offset may mean that the center longitudinal axis of the inner member is spaced apart or generally coplanar with a center longitudinal axis of the outer member in a vertical direction or along a vertical axis; in a lateral or transverse direction or along a lateral or transverse axis; or in a direction or along an axis therebetween.

Inner member. The inner member may function to cause the jaw assembly to move between an open position and a closed position. The inner member may be an elongated member or beam that is received in the outer member. The inner member may be coaxial to the outer tube. The inner member may be a shaft. The inner member or shaft may be a rod that is solid in cross section. The inner member may be a tube that is hollow. The inner member may have an inner portion that is a slot for receiving the cut blade.

The inner member may be connected at its proximal end to the hand piece or actuation mechanism for moving the inner member. The inner member may be moved proximally to move the jaw assembly between the open position and the closed position. The inner member may be moved distally to move the jaw assembly between the open position and the closed position. The inner member may be moved by manipulating one or more user controls on the hand piece.

At its distal end, the inner member may be connected to one or more jaws. At its distal end, the inner member may include one or more arms or one or more struts. The one or more arms or the one or more struts may connect the inner member to the one or more jaws. The inner member, the one or more arms, or the one or more struts may be connected to the one or more jaws with one or more pivot joints. The inner member may include one or more insulating features to prevent an electrical short if an electrically charged feature such as a jaw or cut blade make contact with the inner member.

Struts of outer member. The outer member may include one or more struts. The one or more struts may function to connect the outer member to the one or more jaws. The one or more struts may function to hold or maintain one or more pivot joints. The one or more struts may be rigid anchors that extend from a distal end of the outer member. The one or more struts may be integrally formed with the outer member as a single monolithic member. The one or more struts may cantilever or extend from a distal end of the outer member. Cantilever may mean that the one or more struts are connected to the outer member in a manner such that all six degrees of freedom (conventionally defined as translations along the x-axis, y-axis and z-axis, and rotation about the x-axis, y-axis and z-axis) of the struts are constrained relative to the outer member. The one or more struts may be discrete components that are connected or attached to the outer member. During movement of the jaw assembly between the open and closed position, the one or more struts do not move, or are free of moving, independently relative to the outer member.

The outer member may include any number of struts. For example, the outer member may include two struts. The two struts may oppose one another. The struts may be located lateral or transverse to a central longitudinal axis of the outer member, inner member, cut blade, or a combination thereof. The struts of the outer member may be aligned together and generally oppose each other along a transverse or lateral axis or plane. The one or more struts may be rigid. The one or more struts may be rigid members or links.

Arms of the Inner Member. The inner member may include one or more arms. The one or more arms of the inner member may function to connect the inner member to the one or more jaws. The one or more arms of the inner member may function to hold or maintain one or more pivot joints. The one or more arms may be integrally formed with the inner member as a single monolithic member.

During movement of the jaw assembly between the open and closed position, the one or more arms, or portions of the one or more arms of the inner member, may move independently relative to the rest of the inner member. Moveable may mean that the one or more arms, or portions of the one or more arms, can be moved, bent, articulated, deflected, repositioned, flexed, biased, rotated, pivoted, displaced, the like, or a combination thereof towards or away from, or relative to any axis of the instrument. Arms that are pivotable or rotatable are preferably connected to the inner member with a pivot joint, preferably at the proximal end of the arms. Alternatively, arms that are flexible or deformable may be joined to the inner member by a cantilever joint at the proximal end of the arms. The arms of the inner member may move in the vertical plane. For example, the one or more arms of the inner member may move, bend, flex, pivot, and/or extend away from or towards a longitudinal axis of the outer member when the inner member is moved, when the jaw assembly is moved between an open and closed position (or a closed and open position), or both. A distal end of each of the one or more arms of the inner member may be displaced towards or away from an axis when the jaw assembly is moved from a closed position towards an open position, or vice versa, while a proximal end of each arm generally does not move (e.g. the proximal of each arm might be connected to the inner member by a pivot joint or a cantilevered joint). Displacement may mean to move from a reference position, without reference to any stored spring energy in the arms.

Slots of the outer member. The outer member may include one or more slots. The one or more slots may define an opening, area, or recess in the outer member for the one or more of the arms of the inner member to extend or project through when the jaw assembly is moved from the open position to the closed position and/or from the closed position to the open position. The slot may be a notch, cutout, void, gap, opening, recess, aperture, or a combination thereof defined in the outer member. The one or more slots may be located at a distal end or a distal portion of the outer member. The outer member may include any number of slots. Preferably, the outer member includes the same number of slots as the number of arms of the inner member. For example, if the inner member includes two arms, then the outer member includes two slots. The two slots may generally oppose one another. The slots may be located lateral or transverse to the central longitudinal axis of the outer member and/or located vertically relative to the central longitudinal axis of the outer member.

Struts of inner member. The inner member may include one or more struts. The one or more struts of the inner member may function to connect the inner member to the one or more jaws. The one or more struts may be rigid anchors that extend from a distal end of the inner member, and function to hold or maintain one or more pivot joints. The one or more struts may be integrally formed with the inner member as a single monolithic member. The one or more struts may cantilever or extend from a distal end of the inner member. The one or more struts may be discrete components that are connected or attached to the inner member. During movement of the jaw assembly between the open and closed position, the one or more struts of the inner member do not move, or are free from moving, independently relative to the inner member.

The inner member may include two struts. The two struts may oppose one another. The struts may be located lateral or transverse to a central longitudinal axis of the inner member. The struts of the inner member may be aligned together and generally oppose each other along a transverse or lateral axis or plane. The one or more struts may be rigid. The one or more struts may be rigid members or links.

In some configurations, the inner member may include a single strut. This may be the case if the inner member includes a generally solid or constant cross section. However, the inner member is preferably hollow so that the cutting member can extend through the inner portion of the inner member. Thus, the hollow inner member may include two struts.

Arms of the Outer Member. The outer member may include one or more arms. The one or more arms of the outer member may function to connect the outer member to the one or more jaws. The one or more arms of the outer member may function to hold or maintain one or more pivot joints. The one or more arms may be integrally formed with the outer member as a single monolithic member. An outer member that includes arms is generally free of having struts.

During movement of the jaw assembly between the open and closed position, the one or more arms, or portions of the one or more arms of the outer member move independently relative to the rest of the outer member. Moveable may mean that the one or more arms of the outer member can be moved, bent, articulated, deflected, repositioned, flexed, biased, rotated, pivoted, displaced, the like, or a combination thereof towards or away from, or relative to any axis of the instrument. Arms that are pivotable or rotatable are preferably connected to the outer member with a pivot joint, preferably at the proximal end of the arms. Alternatively, arms that are flexible or deformable may be joined to the inner member by a cantilever joint at the proximal end of hate anus. The arms of the outer member may move in the vertical plane, which may be the plane in which one or both of the jaws move when the jaw assembly is moved between the open and closed position. For example, the one or more arms of the outer member may move, bend, flex, pivot, and/or extend away from or towards a longitudinal axis of the outer member when the inner member is moved, when the jaw assembly is moved between an open and closed position (or a closed and open position), or both. A distal end of each of the one or more arms of the outer member may be displaced towards or away from an axis when the jaw assembly is moved from a closed position towards an open position, or vice versa, while a proximal end of each arm generally does not move. Displacement may mean to move from a reference position, without reference to any stored spring energy in the arms.

Pivot Joint. The instrument may include one or more pivot joints. A pivot joint may function to allow a jaw, strut, and/or arm to move, pivot, or rotate. This description of a pivot joint refers to the pivot joints between the outer member and the jaws and the inner member and the jaws. The pivot joint may be any joint that allows a jaw and/or arm to move, pivot, and/or rotate.

A pivot joint may comprise a pin and one or more slots or openings. The slots of openings may be round and adapted to receive a pin to create a pivot joint. While the figures illustrate the jaws and anus having openings for receiving a pin to complete a pivot joint, it is understood that the pin can be made integral with a jaw or arm as a boss, and the boss can be received in or through one or more openings to complete the pivot joint. One or more of the pivot joints may be coaxial, meaning the joints extend along a common, transverse axis.

One or more of the pivot joints may be carried on the struts of the outer member, the arms of the inner member, or both, so that the one or more pivot joints may be moveable relative to an axis. Moveable may mean that the one or more pivot joints can be moved, repositioned, displaced, the like, or a combination thereof towards or away from, or relative to a jaw closing axis. The one or more pivot joints may be moved when the jaw assembly is moved from the open position towards the closed position, or from the closed position towards the open position. A pivot joint can be located at a distal end or a distal portion of a corresponding arm or strut.

Actuation Mechanism. The instrument may include one or more actuation mechanisms. The actuation mechanism may function to cause the inner member, the jaw assembly, the one or more jaws, or a combination thereof to move. The actuation mechanism may convert or provide movement of the inner member when one or more controls on the hand piece, such as the lever, are moved or manipulated.

For example, when the lever is moved proximally, the actuation mechanism may produce proximal or distal movement of the inner member. For example, when the lever is moved distally, the actuation mechanism may selectively produce proximal or distal movement of the inner member.

When the actuation mechanism produces proximal movement of the inner member, a first jaw may pivot about a pivot joint towards or away from a second jaw, and/or the second jaw may pivot about a pivot joint towards or away from the first jaw. The pivot joints that the first jaw and/or the second jaw pivot about may be the same pivot joint or may be separate, discrete, and different pivot joints.

When the actuation mechanism produces distal movement of the inner member, a first jaw may pivot about a pivot joint towards or away from a second jaw, and/or the second jaw may pivot about a pivot joint towards or away from the first jaw. Again, the pivot joints that the first jaw and/or the second jaw pivot about may be the same pivot joint or may be separate, discrete, and different pivot joints.

Jaw Assembly: The instrument may include one or more jaw assemblies. The jaw assembly may be configured to perform, one or more effecting functions. For example, the one or more effecting functions may include: capturing an object or anatomical feature; grasping an object or anatomical feature; providing a clamping force to secure an object or anatomical feature; providing retraction of an object or anatomical feature; providing a compression force across an object or anatomical feature captured in the jaw assembly; or a combination thereof. The anatomical feature may be, for example, a vessel, tissue, vein, artery, a portion of the anatomy, or a combination thereof. The jaw assembly may be used in electrosurgery to perform one or more electrically effecting functions, such as cutting, coagulating, cauterizing, dissecting, and/or fulgurating an object anatomical feature.

The jaw assembly may be moved between a closed position and an open position. The open position may be a steady state position, and the jaw assembly may be moved from the open position to the closed position by manipulating one or more user controls on the hand piece, such as the lever. When moving to the closed position, one jaw may move towards the other jaw, or both jaws may move towards each other. That is, one jaw may move towards the other jaw by rotating about a pivot joint, or both jaws may move towards each other by rotating about the same pivot joint or different point joints. The jaw assembly can be moved between the open position and the closed position by moving the inner member, and/or the outer member.

The closed position of the jaw assembly may be defined as a position of the jaws or the jaw assembly where virtually no gap, or only a slight gap, exists between the gripping sections, the electrically conductive sections, the jaws, or a combination thereof. In the closed position, a clamping or gripping force of the gripping sections, the electrically conductive portions, the jaws, or a combination thereof may be higher or larger than a clamping or gripping force between the gripping sections, the electrically conductive sections, the jaws, or a combination thereof when the jaws are in the open position.

The open position of the jaw assembly may be defined as a position of the jaws or the jaw assembly where the jaws are spaced apart and an anatomical feature can be placed between the opposing jaws. In the open position, a clamping or gripping force of the gripping sections, the electrically conductive portions, the jaws, or a combination thereof may be lower or less than a clamping or gripping force between the gripping sections, the electrically conductive sections, the jaws, or a combination thereof when the jaws are in the closed position. When moving to the open, position, one jaw may move away from the other jaw, or both jaws may move away from each other. That is, one jaw may move away from the other jaw by rotating about a pivot joint, or both jaws may move away from each other by rotating about the same pivot joint or different point joints. The jaw assembly can be moved between the open position and the closed position by moving the inner member, and/or the outer member.

While the jaw assembly is in an open position. closed position, or in a position there between, the jaw assembly can be rotated about a longitudinal axis of the inner member relative to the hand piece. Rotating the jaw assembly, may provide for a user to alter an orientation or approach of the jaw assembly relative to an object, vessel or tissue without having to twist or adjust the hand piece into a difficult or uncomfortable position. To rotate the jaw assembly, a user can manipulate or actuate one or more controls on the hand piece, such as turning or rotating a rotation wheel on the hand piece, for example, so that the inner member and the outer member rotate.

Jaws. The jaw assembly may include one or more jaws. The jaws may be moved, adjusted, manipulated, repositioned, opened, closed, rotated, to perform one or more effecting functions. The jaws may be moved, adjusted, manipulated, repositioned, rotated, when the jaw assembly is moved between the open and dosed positions. The jaws may be moved, adjusted, manipulated, repositioned, opened, closed, rotated, with one of the user controls on the hand piece. First jaw may be used interchangeably herein with upper jaw or lower jaw. Second jaw may be used interchangeably herein with upper jaw or lower jaw.

The jaws may oppose one another. The jaws may include a first or upper jaw and an identical second or lower jaw. Alternatively, the opposing jaws need not be identical. In other words, the geometry of the upper jaw may be different from the lower jaw. The jaws may be substantially rigid; substantially flexible; substantially resilient, or a combination thereof. That is, the jaws may have one or more sections that are substantially rigid; one or more sections that are substantially flexible; one or more sections that are substantially resilient, or a combination thereof.

The jaws may be fabricated from any suitable material. Preferably, the jaws are fabricated from a material that is suitable for use in medical procedures, and is rigid. For example, the jaw elements may be made from sheet metal or wire. The jaws may be formed by any suitable process, such as stamping, metal injection molding (MIM), or plastic injection molding, for example. The jaws may be fabricated from a material that can pass current so that one or more of the jaws can be used in electrosurgery. One or both of the jaws, or sections thereof, may be electrically conductive. One or both jaws, or sections thereof, may be non-electrically conductive. The jaws may be thermally insulating so that a thermal barrier can be provided between the jaws, the jaw assembly, or both. A thermally insulting jaw may be preferred in some applications so that thermal spread is limited or reduced. One or more sections of the jaws may be covered or coated in an insulating material so that electrical shorts can be prevented if the jaws come into contact with one another.

Each of the jaws may be connected to the arms of the inner member or the arms of the outer member with one or more pivot joints. The one or more jaws may include openings for receiving a pin to complete a pivot joint with the corresponding outer or inner member. Alternatively, the one or more jaws may include a boss for connecting to openings in the corresponding outer or inner member.

Gripping Section. The one or more jaws may include one or more gripping sections. The gripping sections may function to effect an object or anatomical feature manipulate. The one or more gripping sections may be located at or near a distal region of a jaw.

The one or more gripping sections may include one or more areas having teeth, no teeth, projections, or a combination thereof. The one or more teeth or projections may be formed or cut into the jaw or gripping section by a suitable process or method, such as by grinding, electrical discharge machining, stamping, coining, etc. The gripping section may include one or more troughs between the teeth to separate one tooth from another. The one or more teeth may have sharp points to assist in grasping an object or tissue. Alternatively, or in addition, the one or more teeth may have flattened tops to distribute forces associated with grasping forces so that the object or tissue, especially vessel walls, are not punctured or otherwise damaged when an object, vessel, or tissue is between the jaws in the closed position.

The gripping section may be electrically conductive. That is, the gripping section may include one or more electrically conductive sections. The electrically conductive section may function to pass one or more therapy signals or currents between the gripping section, electrically conductive section, an object, the anatomy, or a combination thereof. The electrically conductive section may be, or may include, an electrode that is in communication with a power source. The electrically conductive may be an entire portion of the gripping section. That is, the electrically conductive sections may extend in an area or region between a distal tip of a jaw and a distal portion of an arcuate section. The electrically conductive sections may comprise a smaller area or section than the entire gripping section.

The gripping section may include one or more insulated sections or non-electrically conductive sections. The one or more insulated or non-electrically conductive sections may be insulated or otherwise not connected to an electrode or power source. Accordingly, the one or more non-electrically conductive sections may be unable or restricted from passing a therapy current between the jaws, an object, the anatomy, or a combination thereof.

Cut Blade. The instrument may include one or more cut blades. The cut blade may function to cut an object or anatomical feature of interest, such as a vessel or tissue, for example. The cut blade may be a cutting blade, scalpel, etc. The cut blade can be located between the jaws. The cut blade can be located in a slot defined in one or both of the jaws. The cut blade may be centered on or about a longitudinal axis of one or both of the jaws, the outer member, the inner member, or a combination thereof. Alternatively, the cut blade may be centered on or about an axis that is offset or spaced laterally from a longitudinal axis of one or both of the jaws, the outer member, the inner member, or a combination thereof. The cut blade may be received in the inner member, which is received in the outer member. Alternatively, the cut Glade can be arranged adjacent the inner member inside the outer member.

The cut blade may be repositioned or reciprocated by manipulating one or more of the user controls on the hand piece. The cut blade can be moved or extended to cut an object, vessel or tissue captured between the jaw assembly (e.g., when the jaw assembly is in a closed or clamping position). The cut blade may be electrically conductive. The cut blade may be connected to the power source and used in electrosurgery. Alternatively, the cut blade can be non-participating in an electrical circuit and used as a mechanical or cold cut blade.

FIG. 1 illustrates an instrument 10. The instrument 10 includes a tubular Outer member 12, a jaw assembly 14, and a hand piece 16. The instrument 10 includes an inner member 18 received in the outer member 12, and a cut blade 20 received in the inner member 18.

The jaw assembly 14 comprises a first jaw 22 and a second jaw 24. The hand piece 16 includes a handle 26 for grasping the instrument 10, and one or mote controls, including a lever 28, a trigger 30, a wheel 32, and a button 34.

Figure 4:
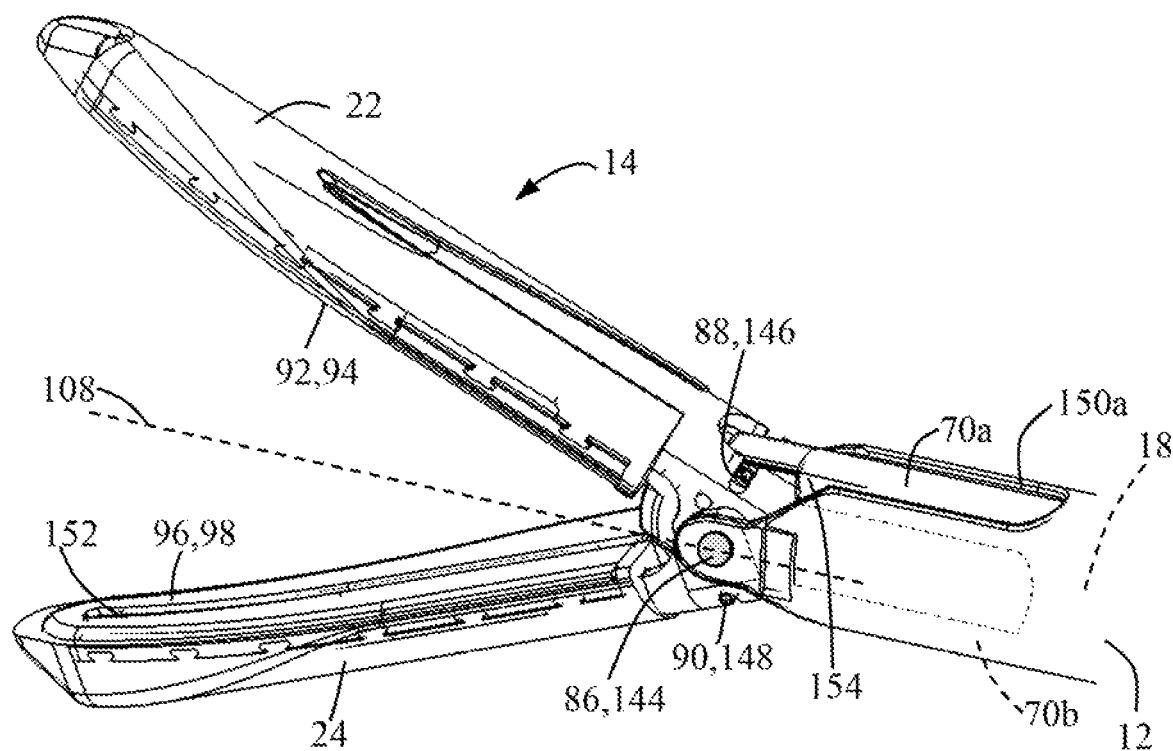
FIG. 4 is a perspective view of the jaw assembly in the open position.
Figure 5:
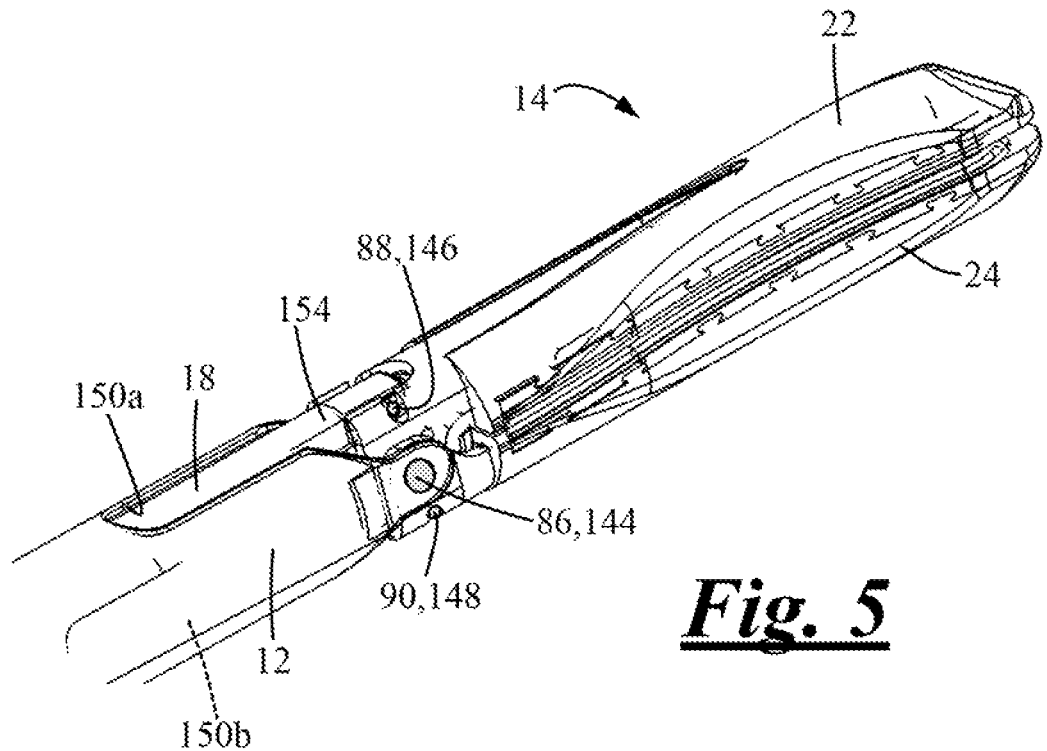
FIG. 5 is a perspective view of the jaw assembly in the closed position.

The lever 28 can be moved or actuated to move the jaw assembly 14 between an open position (FIGS. 1, 3, 4, and 6) and a closed position (FIG. 5). The trigger 30 can be moved or actuated to move the cut blade 20. The jaw assembly 14 can be rotated about a longitudinal axis 108 by turning the wheel 32. The instrument 10 may be in communication with a power source 36. Moving or actuating the button 34 may provide a therapy current supplied by the power source 36 to or between one or both of the jaws 22, 24 and/or electrodes located on one or both of the jaws 22, 24 and/or at a remote location such as a remote pad.

The instrument 10 includes an actuation mechanism 38. The actuation mechanism 38 functions to convert movement of the lever 28 relative to the handle 26 into movement of the inner member 18, which causes the jaw assembly 14 to move between an open position and a closed position. In the open position, the jaws 22, 24 are spaced apart from one another. One or both of the jaws 22, 24 can be moved towards each other into the closed position where the gap between the jaws 22, 24 is reduced or eliminated.

Figure 2:
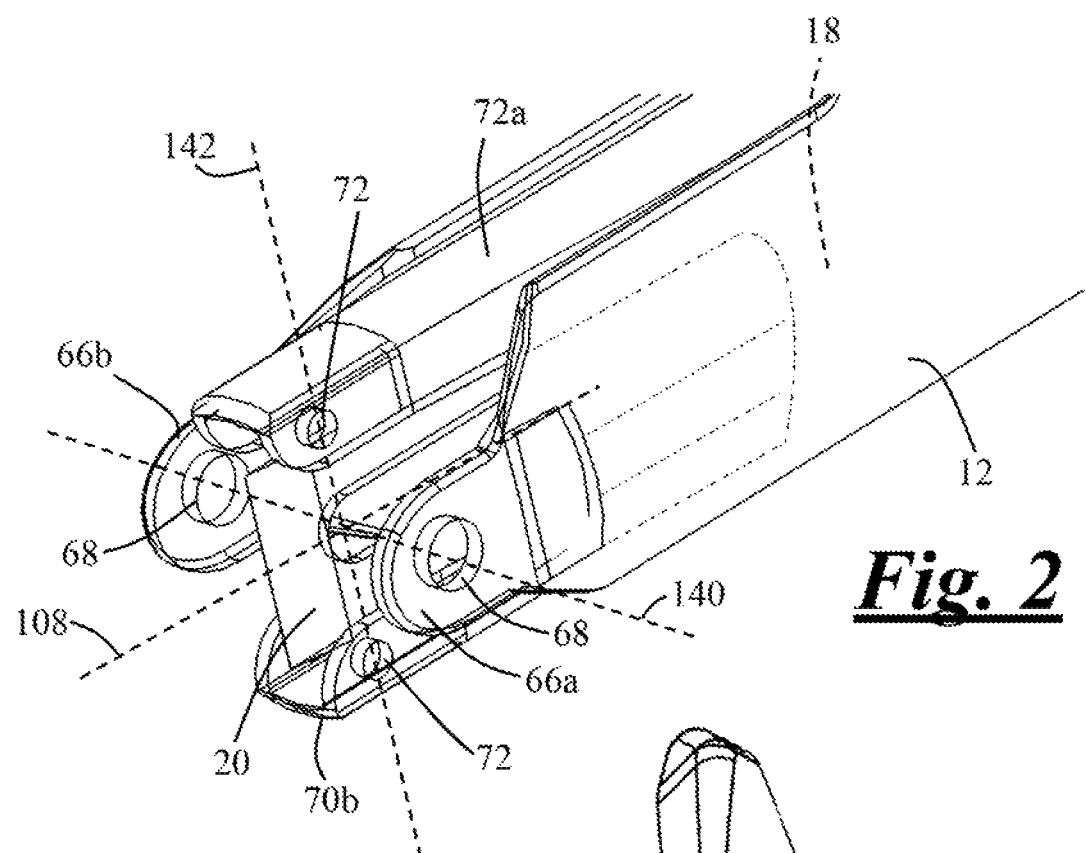
FIG. 2 is a partial perspective of the distal end of the outer member and the inner member.

FIG. 2 illustrates a distal end of the outer member 12, a distal end of the inner member 18, and a distal end of the cut blade 20. A pair of rigid struts 66a, 66b extend or cantilever from the distal end of the outer member 12. The struts 66a, 66b may be generally aligned along or centered about a transverse axis 140, and may be located on opposite sides of a central plane or a jaw closing plane that is defined by the intersection of the vertical axis 142 and the longitudinal axis 108. The transverse axis 140 extends cross-wise across the jaws or a gripping section of the jaw assembly 14. Each of the struts 66a, 66b include an opening 68, The openings 68 in the struts 66a, 66b may be aligned along the transverse axis 140, and may be located on opposite sides of the vertical axis 142 and/or the longitudinal axis 108.

With continued reference to FIG. 2, a pair of moveable arms 70a, 70b extend from a distal end of the inner member 18. The arms 70a, 70b may be integrally formed with or connected to a distal end of the inner member 18. The arms 70a, 70b may be generally aligned along a vertical axis 142, and may be located on opposite sides of the longitudinal axis 108. Each of the arms 70a, 70b include an opening 72. The openings 72 in the arms 70a, 70b may be aligned along a vertical axis 142 and also located on opposite sides of the longitudinal axis 108 and/or the transverse axis 140.

Figure 3:
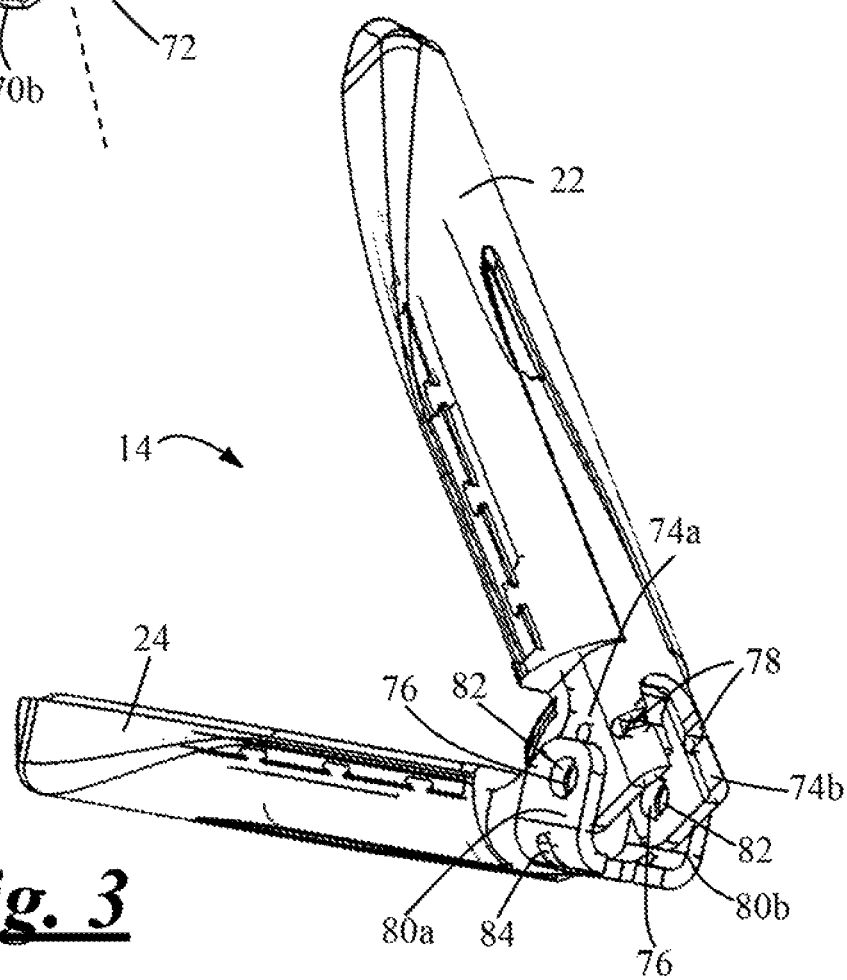
FIG. 3 is a perspective of the jaw assembly in the open position.

FIG. 3 illustrates the jaw assembly 14. The first jaw 22 includes a pair of arms 74a, 74b. Each arm 74a, 74b includes an opening 76. A slot 78 extends through both arms 74a, 74b, The second jaw 24 includes a pair of arms 80a, 80b. Each arm 80a, 80b includes an, opening 82. A slot 84 extends through both arms 80a, 80b.

While FIG. 3 illustrates the arms 74a, 74b of the first jaw 22 being located or nested between the arms 80a, 80b, it is understood that the arms 80a, 80b can be nested between the arms 74a, 74b. Moreover, rather than both arms of one of the jaws 22, 24 being nested between the arms of the other jaw 22, 24, the arms may be staggered. Staggered may mean that one or the arms 74a, 74b is located between or medial to both of arms 80a, 80b, while the other arm 74a, 74h is located outside or lateral of one of the arms 80a, 80b.

FIG. 4 illustrates the jaw assembly 14 in the open position. FIG. 5 illustrates the jaw assembly 14 in the closed position.

Referring to both FIGS. 4 and 5, along with FIGS. 2 and 3, a pin 86 extends through the openings 68 in the struts 66a, 66b, the openings 76 in the arms 74a, 74b of the first, aw 22, and the openings 82 in the arms 80a, 80b of the second jaw 24 thereby connecting the first jaw 22, the second jaw 24, and the outer member 12 at a pivot joint 144.

Pivot joint 144 may be referred to as two pivot joints—that is, a first pivot joint that connects jaw 22 and arm 74a of the inner member 18 and another pivot joint that connects jaw 24 and arm 74b of the inner member. However, both of these aforementioned pivot joints that make up pivot joint 144 pivot about the same axis and may use the same pin 86 to connect the respective jaws and arms.

Another pin 88 extends through the opening 72 of arm 70a of the inner member 18 and the slot 78 of the first jaw 22 thereby connecting jaw 22 to the arm 70a to the inner member 18 at a pivot joint 146.

Another pin 90 extends through the opening 72 in the arm 70b of the inner member 18 and the slot 84 of the second jaw 24 thereby connecting jaw 24 to the arm 70b to the inner member 18 at a pivot joint 148.

At its distal end, the outer member 12 includes a first notch or cutout 150a corresponding to the arm 70a of the inner member 1 8, and a second notch or cutout 150b corresponding to the arm 70b of the inner member 18. The notches 150a, 150b are defined between the opposing struts 66a, 66b.

When the inner member 18 is advanced distally relative to the stationary outer member 12, by, for example, manipulating, moving, or grasping the lever 28 (FIG. 1), which causes the actuation mechanism 38 to move the inner member 18 distally relative to the stationary outer member 12 and/or handle 26, jaw 22 pivots at the pivot joint 144 towards jaw 24, and, jaw 24 pivots at the pivot joint 144 towards jaw 22 until the jaw assembly 14 is in the closed position.

Moreover, when the inner member 18 is advanced distally relative to the stationary outer member 12, a distal portion 154 of the arm 70a of the inner member 18 displaces, or moves either towards or away from, the longitudinal axis 108 such that the distal portion 154 of the arm 70a extends through the notch or cutout 150a.

Similarly, while not shown in FIG. 4, when the inner member 18 is advanced distally relative to the stationary outer member 12, a distal portion of the arm 70b of the inner member 18 displaces, or moves either towards or away from, the longitudinal axis 108 such that the distal portion of the arm 70b extends through the notch or cutout 150b.

When the inner member 18 is moved or retracted proximally relative to the stationary outer member 12 by, for example, manipulating, moving, or releasing the lever 28 (FIG. 1), which causes the actuation mechanism 38 to move the inner member 18 proximally relative to the stationary outer member 12 and/or handle 26, the jaw 22 pivots at the pivot joint 144 away from jaw 24, and, jaw 24 pivots at the pivot joint 144 away from jaw 22 until the jaw assembly 14 is back in the open position.

When the inner member 18 is moved, or retracted proximally relative to the stationary outer member 12, the distal portion 154 of the arm 70a of the inner member 18 displaces, or moves either towards or away from the longitudinal axis 108 and back into or within the notch or cutout 150a. Similarly, the distal portion of the arm 70b of the inner member 18 displaces or moves either towards or away from the longitudinal axis 108 and back into or within the notch or cutout 150b when the inner member 18 is moved or retracted proximally relative to the stationary outer member 12.

The first jaw 22 includes a gripping section 92. The gripping section 92 may be electrically conductive, and may be in communication with the power source 36. Additionally, or alternatively, the gripping section 92 may include an electrode 94 that is in electrical communication with the power source 36.

The second jaw 24 includes a gripping section 96. The gripping section 96 may be electrically conductive, and may be in communication with the power source 36. Additionally, or alternatively, the gripping section 96 may include an electrode 98 that is in electrical communication with the power source 36.

One or both of the jaws 22, 24 may include a cut blade slot 152 for the cut blade 20 to extend along when the cut blade 20 is extended and retracted by, for example, moving or manipulating the trigger 30 (FIG. 1).

Figure 6:
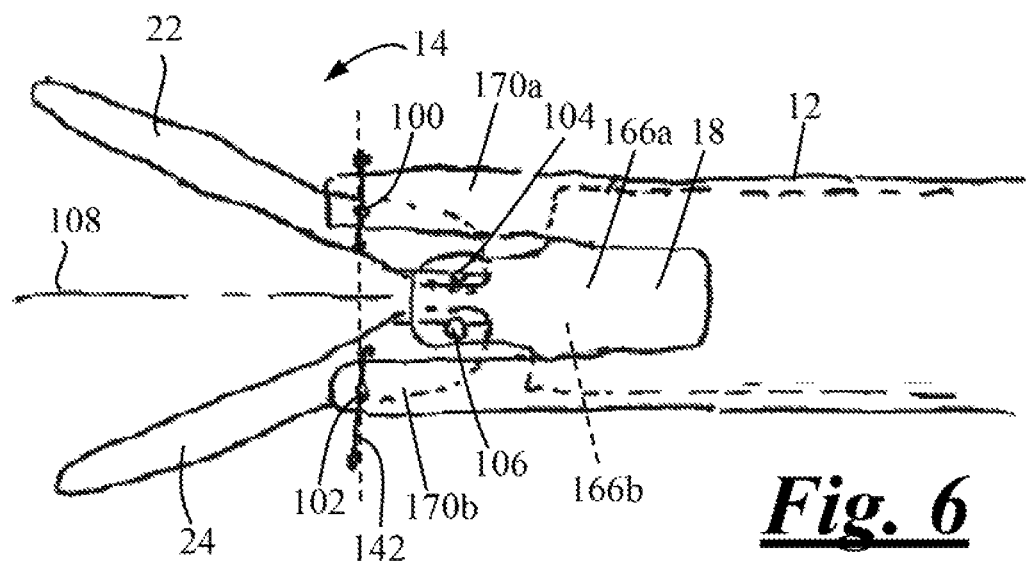
FIG. 6 is a side view of the jaw assembly, and a distal portion of the inner member and the outer member.

FIG. 6 illustrates the jaw assembly 14 in the open position. Opposing moveable arms 170a, 170 extend or cantilever from a distal end of the outer member 12. The arms 170a, 170b are generally aligned along the vertical axis 142, and are located on opposite sides of the longitudinal axis 108. The arms 170a, 170b are flexible and resilient. Jaw 22 is connected to arm 170a at pivot joint 100, and jaw 24 is connected to arm 170b at pivot joint 102. Pivot joints 100 and 102 are generally aligned along the vertical axis 142, and are located on opposite sides of the longitudinal axis 108.

In FIG. 6, a pair of rigid struts 166a, 166b extend or cantilever from a distal end of the inner member 18. The struts 166a, 166b are offset or located on opposite sides of the central jaw opening plane in a transverse or lateral direction. It is understood that if the inner member 18 were to include a substantially solid cross section, then these struts 166a, 166b may not exist however, the inner member 18 would still preferably include openings 104, 106 discussed further below. However, because the inner member 18 is preferably hollow, the inner member includes the struts 166a, 166b that extend from a distal end thereof.

In FIG. 6, the jaw 22 is connected to the strut 170a of inner member 18 at pivot joint 104, and jaw 24 is connected to the strut 170b at pivot joint 106, Pivot joints 104 and 106 are generally aligned along the vertical axis 142, and are located on opposite sides of the longitudinal axis 108. It is understood that pivot joints 104 and 106 can be arranged to be coaxial or can be a single, common pivot joint. Pivot joints 104, 106 are located between pivot joints 100 and 102. This means that pivot joints 104, 106 are located closer to the longitudinal axis 108 than pivot joints 100, 102. Accordingly, pivot joints 104, 106 are located farther away from the longitudinal axis 108 than pivot joints 100, 102. Also, as can be clearly seen in this figure, pivot joints 100 and 104 are located on a first side of the longitudinal axis 108, and pivot joints 102 and 106 are located on a second side of the longitudinal axis 108.

In FIG. 6, when the inner member 18 is retracted in a proximal direction, for example by moving or manipulating the lever 28 relative to the handle 26, which causes the actuation mechanism 38 to move the inner member in a proximal direction relative to the stationary outer member 12 and hand piece 16, the jaws 22, 24 rotate or pivot about the pivot joints 104, 106 towards each other from the illustrated open position to the closed position. The arms 170a, 170b are flexible so that during closing of the jaw assembly 14, the 170a, 170b move, flex, or bend towards the center axis 106 thus allowing the instrument 10, the jaws 22, 24, the inner member 18, or a combination thereof to move without providing binding. Moreover, as illustrated in FIG. 6, pivots 100 and 102 are located distal of pivots 104 and 106 so that when the jaws 22, 24 rotate towards each other into a closed position, the pivots 100 and 102 only move towards the longitudinal axis 108.

In FIG. 6, when the inner member is moved or advanced in a distal direction, for example by moving or manipulating the lever 28 relative to the handle 26, which causes the actuation mechanism 38 to move the inner member in a distal direction relative to the stationary outer member 12 and hand piece 16, the jaws 22, 24 rotate about the pivot joints 100, 102, from the closed position back to the open illustrated position. During this movement, the anus 170a, 170b relax, flex, or bend back to their steady state position away from the center axis 108.

Figure 7:
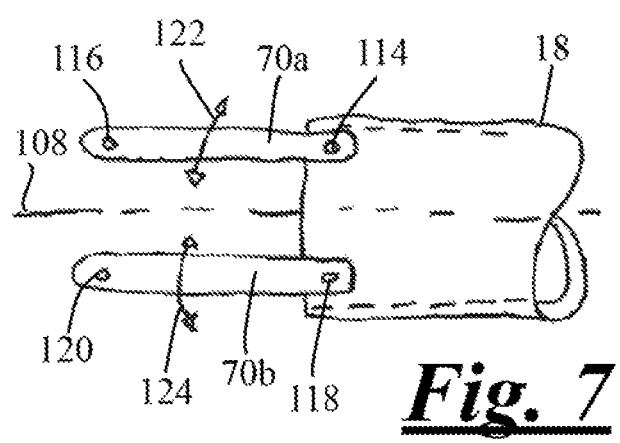
FIG. 7 is a side view of a distal portion of the inner member.

FIG. 7 illustrates a distal portion of the inner member 18. Arm 70a is a discrete component or link that is connected at its proximal end to the inner member 18 at a pivot joint 114. At its distal end, arm 70a is connected to jaw 22 (not illustrated) via pivot joint 116. Similarly, arm 70b is a discrete component or link that is connected at its proximal end to the inner member 18 via a pivot joint 118. At its distal end, arm 70b is connected to jaw 24 (not illustrated) via pivot joint 120. Pivot joints 114, 116 allow lateral movement of the arms 70a, 70b along the respective axes 122, 124 as the jaws 22, 24 rotate between the open and closed position.

FIG. 7 may also illustrate a distal portion of the outer member. In other words, while reference numbers are not provided for the following description, it is contemplated that the structure illustrated in FIG. 7 may be an outer member 12 that is used with the inner member 12 illustrated and described in FIG. 6, for example. In other words, rather than having arms 170a, 170b of the outer member 12 that move, bend, or flex towards and away from the center axis 108 during opening and closing of the jaw assembly 14 like those illustrated and described at FIG. 6, the arms 170a, 170b of the outer member 12 may instead be rigid links that pivot about the pivot joints 114, 118 illustrated in FIG. 7 so that the arms 170a, 170b move laterally along the respective axes 122, 124 as the jaws 22, 24, that are connected to the respective anus 170a, 170b at pivots 116, 120, rotate between the open and closed position.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The disclosures of all articles and references, including patent applications and publications, are incorporated by reference for all purposes. Plural elements or steps can be provided by a single integrated element or step. Alternatively, a single element or step might be divided into separate plural elements or steps. The disclosure of "a" or "one" to describe an element or step is not intended to foreclose additional elements or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter nor should it be regarded that the inventors did not consider such subject matter to be part of the disclosed inventive subject matter.

The invention claimed is:

1. An instrument comprising:
    a) an outer member that extends along a longitudinal axis;
    b) an inner member received in the outer member, the inner member comprising:
        i) a first moveable arm; and
        ii) a second moveable arm;
    c) a jaw assembly that is moveable between an open position and a closed position, the jaw assembly comprising:
        i) a first jaw; and
        ii) a second jaw;
    wherein the first jaw is connected to the first moveable arm at a first pivot joint, the first jaw is connected to the outer member at a second pivot joint;
    wherein the second jaw is connected to the second moveable arm at a third pivot joint, the second jaw is connected to the outer member at a fourth pivot joint;
    wherein the second pivot joint and the fourth pivot joint are located on opposite sides of the longitudinal axis, and both the second pivot joint and the fourth pivot joint are aligned along a horizontal axis that extends generally perpendicular to the longitudinal axis;
    wherein the inner member is adapted to be moved distally relative to the outer member so that the first jaw pivots about the second pivot joint towards the second jaw and the second jaw pivots about the fourth pivot joint towards the first jaw thus moving the jaw assembly from the open position towards the closed position,
    wherein a proximal end of the first moveable arm and a proximal end of the second movable arm each cantilever from a distal end of the inner member;
    wherein a distal end of the first moveable arm and a distal end of the second movable arm both displace relative to the longitudinal axis when the jaw assembly is moved from the closed position toward the open position;
    wherein the distal end of the first moveable arm and the distal end of the second movable arm both displace relative to the longitudinal axis when the jaw assembly is moved from the open position toward the closed position,
    wherein the first moveable arm and the second movable arm are bendable;
    wherein both the first moveable arm and the second movable arm bend towards the longitudinal axis when the jaw assembly is moved from the open position toward the closed position;
    wherein the first moveable arm and the second movable arm both bend away from the longitudinal axis when the jaw assembly is moved from the closed position to the open position.

2. The instrument of claim 1, wherein the instrument comprises a hand piece that includes a lever and a handle, and
    wherein the lever is adapted to be moved relative to the handle so that the inner member is moved proximally relative to the outer member so that the first jaw pivots about the second pivot joint away from the second jaw and the second jaw pivots about the fourth pivot joint away from the first jaw thus moving the jaw assembly from the closed position towards the open position.

3. The instrument of claim 1, wherein both the first pivot joint and the third pivot joint displace relative to the longitudinal axis when the jaw assembly is rotated from the closed position toward the open position.

4. The instrument of claim 1, wherein the outer member includes a first slot and a second slot, the first slot is adjacent the first moveable arm and the second slot is adjacent the second movable arm; and
    wherein the first moveable arm extends through the first slot when the first jaw pivots away from the second jaw, and the second movable arm extends through the second slot when the second jaw pivots away from the first jaw.

5. The instrument of claim 1, wherein the first moveable arm has a C-shaped cross section, and the second movable arm has a C-shaped cross section.

6. The instrument of claim 5, wherein the instrument comprises a cut blade that is located between the C-shaped cross section of the first moveable arm and the C-shaped cross section of the second moveable arm.

7. An instrument comprising:
    a) an outer member that extends along a longitudinal axis:
    b) an inner member received in the outer member, the inner member comprising:
        i) a first moveable arm having a C-shaped cross section that extends from a distal end of the inner member; and
        ii) a second moveable arm having a C-shaped cross section that extends from the distal end of the inner member;
    c) a cut blade that is located between the C-shaped cross section of the first moveable arm and the C-shaped cross section of the second moveable arm; and d) a jaw assembly that is moveable between an open position and a closed position, the jaw assembly comprising:
   i) a first jaw; and
   ii) a second jaw;
wherein the first jaw is connected to the first moveable arm at a first pivot joint, the first jaw is connected to the outer member at a second pivot joint;
wherein the second jaw is connected to the second moveable arm at a third pivot joint, the second jaw is connected to the outer member at a fourth pivot joint;
wherein the inner member is adapted to be moved distally relative to the outer member so that the first jaw pivots about the second pivot joint towards the second jaw and the second jaw pivots about the fourth pivot joint towards the first jaw thus moving the jaw assembly from the open position towards the closed position; and
wherein both of the second pivot joint and the fourth pivot joint are located in between the first pivot joint and the third pivot joint.

8. An instrument comprising:
a) an outer member that extends along a longitudinal axis:
b) an inner member received in the outer member, the inner member comprising:
   i) a first moveable arm having a C-shaped cross section that extends from a distal end of the inner member; and
   ii) a second moveable arm having a C-shaped cross section that extends from the distal end of the inner member;
c) a cut blade that is located between the C-shaped cross section of the first moveable arm and the C shaped cross section of the second moveable arm; and
d) a jaw assembly that is moveable between an open position and a closed position, the jaw assembly comprising:
   i) a first jaw; and
   ii) a second jaw;
wherein the first jaw is connected to the first moveable arm at a first pivot joint, the first jaw is connected to the outer member at a second pivot joint;
wherein the second jaw is connected to the second moveable arm at a third pivot joint, the second jaw is connected to the outer member at a fourth pivot joint;
wherein the inner member is adapted to be moved distally relative to the outer member so that the first jaw pivots about the second pivot joint towards the second jaw and the second jaw pivots about the fourth pivot joint towards the first jaw thus moving the jaw assembly from the open position towards the closed position;
wherein the instrument comprises a hand piece that includes a lever and a handle;
wherein the lever is adapted to be moved relative to the handle so that the inner member is moved proximally relative to the outer member so that the first jaw pivots about the second pivot joint away from the second jaw and the second jaw pivots about the fourth pivot joint away from the first jaw thus moving the jaw assembly from the closed position to the open position;
wherein the first moveable arm and the second movable arm are both bendable;
wherein the first moveable arm and the second movable arm bend away from the longitudinal axis when the jaw assembly is moved from the closed position to the open position; and wherein the first moveable arm and the second movable arm bend towards the longitudinal axis when the jaw assembly is moved from the open position to the closed position.

9. An instrument comprising: a) an outer member that extends along a longitudinal axis: b) an inner member received in the outer member, the inner member comprising: i) a first moveable arm having a C-shaped cross section that extends from a distal end of the inner member; and ii) a second moveable arm having a C-shaped cross section that extends from the distal end of the inner member, c) a cut blade that is located between the C-shaped cross section of the first moveable arm and the C-shaped cross section of the second moveable arm, and d) a jaw assembly that is moveable between an open position and a closed position, the jaw assembly comprising; i) a first jaw; and ii) a second jaw, wherein the first jaw is connected to the first moveable arm at a first pivot joint, the first jaw is connected to the outer member at a second pivot joint; wherein the second jaw is connected to the second movable arm at a third pivot joint, the second jaw is connected to the outer member at a fourth pivot joint, wherein the inner member is adapted to be moved distally relative to the outer member so that the first jaw pivots about the second pivot joint towards the second jaw and the second jaw pivots about the fourth pivot joint towards the first jaw thus moving the jaw assembly from the open position towards the closed position; wherein the first pivot joint comprises a first opening defined in the first moveable arm and a first pin extending through the first opening, and the third pivot joint comprises a second opening defined in the second movable arm and a second pin extending through the second opening defined in the second movable arm, and wherein the cut blade is reciprocated in between the first pin and the second pin.

10. The instrument of claim 9, wherein the second pivot joint comprises a third pin that extends through a third opening defined in the outer member, and the cut blade comprises a slot through which the third pin extends.

11. The instrument of claim 9, wherein the cut blade that is configured to reciprocate between the C-shaped cross section of the first moveable arm and the C-shaped cross section of the second moveable arm.

12. An instrument comprising:
a) an outer member that extends along a longitudinal axis:
b) an inner member received in the outer member, the inner member comprising:
   i) a first moveable arm having a C-shaped cross section that extends from a distal end of the inner member; and
   ii) a second moveable arm having a C-shaped cross section that extends from the distal end of the inner member;
c) a cut blade that is located between the C-shaped cross section of the first moveable arm and the C shaped cross section of the second moveable arm; and
d) a jaw assembly that is moveable between an open position and a closed position, the jaw assembly comprising:
   i) a first jaw; and
   ii) a second jaw;
wherein the first jaw is connected to the first moveable arm at a first pivot joint, the first jaw is connected to the outer member at a second pivot joint;
wherein the second jaw is connected to the second moveable arm at a third pivot joint, the second jaw is connected to the outer member at a fourth pivot joint;

wherein the inner member is adapted to be moved distally relative to the outer member so that the first jaw pivots about the second pivot joint towards the second jaw and the second jaw pivots about the fourth pivot joint towards the first jaw thus moving the jaw assembly from the open position towards the closed position;

wherein a proximal end of the first jaw comprises C-shaped cross section, and a proximal end of the second jaw comprises a C-shaped cross;

wherein the C-shaped cross section of the first jaw comprises a first pair of arms, and the C-shaped cross section of the second jaw comprises a second pair of arms, wherein the first pair of arms are nested between the second pair of arms.

13. The instrument of claim 12, wherein a proximal end of the first moveable arm and a proximal end of the second movable arm each cantilever from the distal end of the inner member.

14. The instrument of claim 12, wherein the first pivot joint comprises a first pin that extends through a first opening defined in the inner member, and the cut blade comprises a slot.

15. The instrument of claim 14, wherein the second pivot joint comprises a second pin that extends through a second opening defined in the outer member, and the cut blade comprises the slot through which the second pin extends.

16. The instrument of claim 15, wherein the third pivot joint comprises a third opening defined in the second movable arm and a third pin extending through the third opening defined in the second movable arm, wherein the cut blade reciprocates in between the first pin and the third pin.

17. The instrument of claim 12, wherein a proximal end of the first movable arm and a proximal end of the second movable arm each cantilever from the distal end of the inner member.

18. The instrument of claim 12, wherein the cut blade that is configured to reciprocate between the C-shaped cross section of the first moveable arm and the C-shaped cross section of the second moveable arm.

* * * * *

UNITED STATES PATENT AND TRADEMARK OFFICE
CERTIFICATE OF CORRECTION

PATENT NO. : 10,561,433 B2  
APPLICATION NO. : 15/402741  
DATED : February 18, 2020  
INVENTOR(S) : Batchelor et al.

Page 1 of 1

It is certified that error appears in the above-identified patent and that said Letters Patent is hereby corrected as shown below:

On the Title Page

In item (71), in "Applicant", in Column 1, Line 1, after "INC.,", insert --d/b/a Olympus Surgical Technologies America,--

In item (73), in "Assignee", in Column 1, Line 1, delete "Inc.," and insert --Inc. DBA Olympus Surgical Technologies America,-- therefor In the Claims In Column 17, Line 32, in Claim 8, delete "c)a" and insert --c) a-- therefor In Column 17, Line 33, in Claim 8, delete "C shaped" and insert --C-shaped-- therefor In Column 18, Line 9, in Claim 9, delete "member;" and insert --member,-- therefor In Column 18, Line 17, in Claim 9, delete "comprising;" and insert --comprising:-- therefor In Column 18, Line 54, in Claim 12, delete "c)a" and insert --c) a-- therefor In Column 18, Line 55, in Claim 12, delete "C shaped" and insert --C-shaped-- therefor In Column 19, Line 7, in Claim 12, after "comprises", insert --a--

Signed and Sealed this  
Third Day of November, 2020

Andrei Iancu  
*Director of the United States Patent and Trademark Office*